United States Patent [19]

Cale, Jr.

[11] Patent Number: 4,746,657
[45] Date of Patent: May 24, 1988

[54] FUSED AROMATIC TETRAHYDROAZEPINONES (AND THIONES)

[75] Inventor: Albert D. Cale, Jr., Mechanicsville, Va.

[73] Assignee: A. H. Robins Company, Incorporated, Richmond, Va.

[21] Appl. No.: 72,649

[22] Filed: Jul. 13, 1987

[51] Int. Cl.⁴ .................. C07D 223/16; C07D 471/04; A61K 31/55

[52] U.S. Cl. .................... 514/215; 314/213; 540/521; 540/523; 546/275; 548/572

[58] Field of Search ............... 314/213, 215; 540/521, 540/523

[56] References Cited

U.S. PATENT DOCUMENTS 2,785,159  3/1957  Hoffman et al. .................... 540/523

OTHER PUBLICATIONS

Chemical Abstracts, vol 86, (1977) Item 43586p, Abstracting KLAR in Arch. Pharm.(Weinheim, Ger.) (1976) vol. 309, No. 7, pp. 550–557 (German).

Primary Examiner—Robert T. Bond

[57] ABSTRACT

Aromatic tetrahydroazepinones and thoines having the formula:

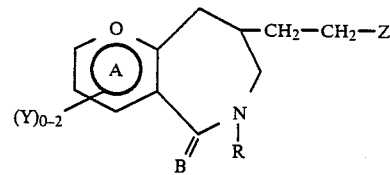

wherein
Q is carbon or nitrogen;
B is oxygen or sulfur;
R is loweralkyl, cycloalkyl or phenylloweralkyl;
Z is an amino or a heterocyclic amino containing radical; and
Y is halo, loweralkyl, loweralkoxy, diloweralkylamino, nitro, phenyl or trifluorophenyl;

and having antihistaminic utility, a process for the preparation thereof and chemical intermediates therefor are disclosed.

9 Claims, No Drawings

FUSED AROMATIC TETRAHYDROAZEPINONES (AND THIONES)

BACKGROUND OF THE INVENTION

1. Field of Invention

The present invention relates to novel aromatic tetrahydroazepinones and sulfur analogs thereof and is particularly concerned with aromatic tetrahydroazepinones and tetrahydroazepinethiones which have the aromatic component fused into the azepine component, each component thereby having two commonly shared carbon atoms and the azepine ring having an oxo (or thioxo) function on the carbon atom adjacent to one of the shared carbon atoms and a short chain aminoalkyl, aklylaminoalkyl or heterocyclicaminoalkyl radical attached to the carbon atom two positions away from the other shared carbon atom, the compounds having antihistaminic and antiallergy utility in a pharmaceutical method and compositions.

2. Information Disclosure Statement

U.S. Pat. No. 4,592,866 discloses aromatic 1,4-oxazepinones, thiazepinones, diazepinones, and thiones of all having antihistaminic utility. The compounds of the present invention differ in that oxygen, sulfur, and nitrogen atoms are absent in the azepine ring and the scope of the aromatic ring is limited to benzo and pyrido having the nitrogen atom fixed in one position. The method of forming the aromatic tetrahydroazepininones in the present instance involving breakup of a pyrrolidine ring and rearrangement is analogous to one method described in that patent for preparing aromatic oxazepininones, thiazepinones and diazepinones. Certain of the novel chemicals used in the synthesis of the azepines of the present invention, i.e., the (N-substituted-pyrrolidinyl)methyl pyridines and benzenes are analogous to pyrrolidinyloxy-, pyrrolidinylthio- and pyrrolidinylaminopyridine (and benzene) carboxylic acids used in the synthesis described in U.S. Pat. No. 4,592,866, the specification of which is hereby incorporated by reference to provide broader scope of synthetic procedures for similar reactions.

OBJECTS AND SUMMARY OF THE INVENTION

The tetrahydroazepinone derivatives of the present invention which exhibit antihistaminic activity have the formula:

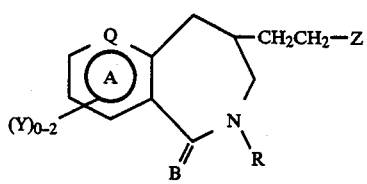

FORMULA I wherein:

A represents an aromatic ring selected from benzo when Q is carbon or from pyrido [3,2-c] when Q is nitrogen, either of which rings may be optionally substituted by one or two Y radicals, the same or different, selected from the group consisting of halo, loweralkyl, loweralkoxy, diloweralkylamino, nitro, phenyl or trifluoromethyl;

B is selected from oxygen or sulfur;

R is selected from the group consisting of loweralkyl, cycloalkyl or phenyl-loweralkyl, wherein phenyl may be optionally substituted by one or two radicals, the same or different, selected from halo, loweralkyl, loweralkoxy, nitro or trifluoromethyl;

Z is selected from the group consisting of $-NR^1R^2$, 1H-pyrazol-1-yl or 1H-imidazol-1-yl;

$R^1$ and $R^2$ may be the same or different and are selected from the group consisting of loweralkyl, cycloalkyl and phenyl-loweralkyl, wherein phenyl may be optionally substituted by 1 or 2 radicals, the same or different, selected from halo, loweralkyl, loweralkoxy, nitro, trifluoromethyl or cyano; or $R^1$ and $R^2$ together with the adjacent nitrogen atom may form a heterocyclic ring structure selected from the group consisting of 1-azetidinyl, 1-pyrrolidinyl, 2,5-dimethyl-1-pyrrolidinyl, 2-methyl-1-pyrrolidinyl, 1-piperidinyl, 4-substituted-1-piperidinyl, 4-[bis(4-fluorophenyl)methyl]-1-piperidinyl, 4-morpholinyl, 1-piperazinyl, 4-substituted-1-piperazinyl, 1,2,3,6-tetrahydropyridin-1-yl, 1H-pyrrol-1-yl or 2,5-dihydro-1H-pyrrol-1-yl;

the optical isomers thereof and the pharmaceutically acceptable salts thereof.

The novel tetrahydroazepine precursors leading to compounds of Formula I have the formula:

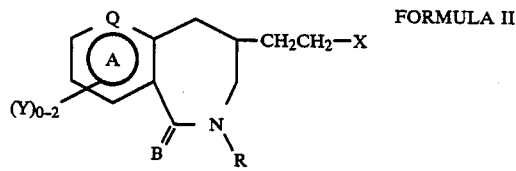

FORMULA II wherein A, B, E, R, Q and Y are as defined under Formula I above and X is chlorine or bromine; the optical isomers thereof and the pharmaceutically acceptable salts thereof.

Other novel chemical intermediates in the preparation of compounds of Formula II have the formula:

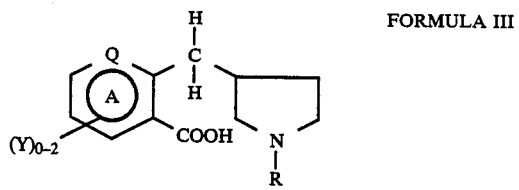

FORMULA III wherein Q is carbon or nitrogen, A, Y and R are as defined above; the optical isomers and the pharmaceutically acceptable salts thereof.

Other novel chemical intermediates in the preparation of compounds of Formula III have the formula:

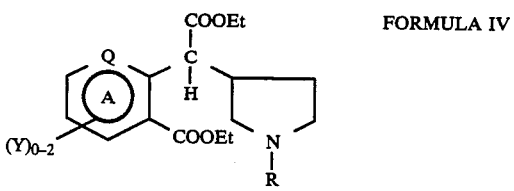

FORMULA IV wherein Q, A, Y and R are as defined above.

In the further definition of symbols in the formulas hereof and where they appear elsewhere throughout this specification and the claims, the terms have the following significance. The term "loweralkyl" as used herein, unless otherwise specified, includes straight and branched chain radicals of up to eight carbons inclusive and is exemplified by such groups as methyl, ethyl, propyl, isopropyl, butyl, sec.butyl, tert.butyl, amyl, isoamyl, hexyl, heptyl and octyl radicals and the like. The term "loweralkoxy" has the formula —O—loweralkyl. The term "diloweralkylamino" has the formula —N(loweralkyl)$_2$. The term "phenyl-loweralkyl" has the formula C$_6$H$_5$—loweralkyl—. The term "loweracylamino" has the formula,

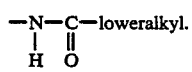

The term "cycloalkyl" as used herein includes primarily cyclic alkyl radicals containing 3–9 carbon atoms inclusive and includes such groups as cyclopropyl, cyclobutyl, cyclopentyl, cyclohexyl, methylcyclohexyl, cycloheptyl and the like.

The terms "halo", "halide" or "halogen" when referred to herein include fluorine, chlorine, bromine and iodine unless otherwise stated.

"Pharmaceutically acceptable salts" include acid addition salts, hydrates, alcoholates and quaternary salts of the compounds of Formula I, which are physiologically compatible in warm-blooded animals. The acid addition salts may be formed by either strong or weak acids. Representatiave of strong acids are hydrochloric, sulfuric and phosphoric acids. Representative of weak acids are fumaric, maleic, succinic, oxalic, citric, tartaric, hexamic, and the like.

Suitable quaternary salts include the loweralkyl halids and loweralkyl sulfates.

By "sulfurizing agent" is meant any agent or mixture of agents which will convert aromatic tetrahydroazepinones, to aromatic tetrahydroazepinethiones, such as 2,4-bis(4-methoxyphenyl)-1,3,2,4-dithiadiphosphetane-2,4-disulfide (Lawesson) reagent or a mixture of phosphorus pentasulfide and alkalimetal sulfide or a mixture of phosphorus pentasulfide in a suitable solvent such as acetonitrile, toluene or pyridine. By the use of "sulfurizing agent" the aromatic tetrahydroazepinones are thereby "sulfurized" to aromatic tetrahydroazepinethiones.

By "4-substituted-1-piperidinyl" is meant a piperidine radical substituted in the 4-position by 1–2 radicals selected from hydroxy, phenyl and phenyl-loweralkyl, wherein phenyl may be substituted by 1–2 halide radicals.

By "4-substituted-1-piperazinyl" is meant a piperazine radical substituted in the 4-position by loweralkyl, alkoxycarbonyl or phenyl radicals.

Compound of Formula I and II have a chiral center in the azepine moiety at the site of the carbon carrying the side-chain and therefore there is potential for separating the enantiomers (optical isomers) or for the synthesis of the enantiomers of compounds of Formula I by using already resolved chemical intermediates of Formula II. Optical isomers may be separated by column chromatography using a column having an appropriate chiral stationary phase or may be resolved with optically active acids.

Compounds of Formula III and IV have a chiral center in the pyrrolidine moiety at the site of the carbon carrying side-chain, therefore there is potential for separation of the enantiomers (optical isomers) or for the synthesis of the enantiomers of compounds of Formula III by using already resolved enantiomers of compounds of Formula IV. Optical isomers may be separated by column chromatography using a column having an appropriate chiral stationary phase, or may be resolved with optically active acids.

The compounds of the present invention exhibit antihistaminic activity in guinea pigs. The method of testing is a modification of the procedure of Tozzi et al. (Agents and Actions, Vol. 4/4, 264–270, 1974) as follows: Guinea pigs are fasted 18–24 hr in individual cages. Water is available ad libitum. On the test day, animals in groups of 3 are injected intraperitoneally with 30 mg/kg of the test compound prepared in an appropriate vehicle. Thirty minutes later histamine at a dosage level of 1.2 mg/kg (=2×the LD$_{99}$) is injected into a marginal ear vein. Survival of the guinea pigs for 24 hr is positive evidence of antihistaminic activity. If the vehicle used for the test compound is other than water, its effect is established by testing an equal amount as a control. The dose protecting 50% of the animals (PD$_{50}$) from death may be established from dose-response curves.

The reaction equations and sequences for preparing compounds of Formulas I, II, III, and IV, as well as starting compounds of Formula V are given in Charts 1, 2, and 3 infra.

CHART 1

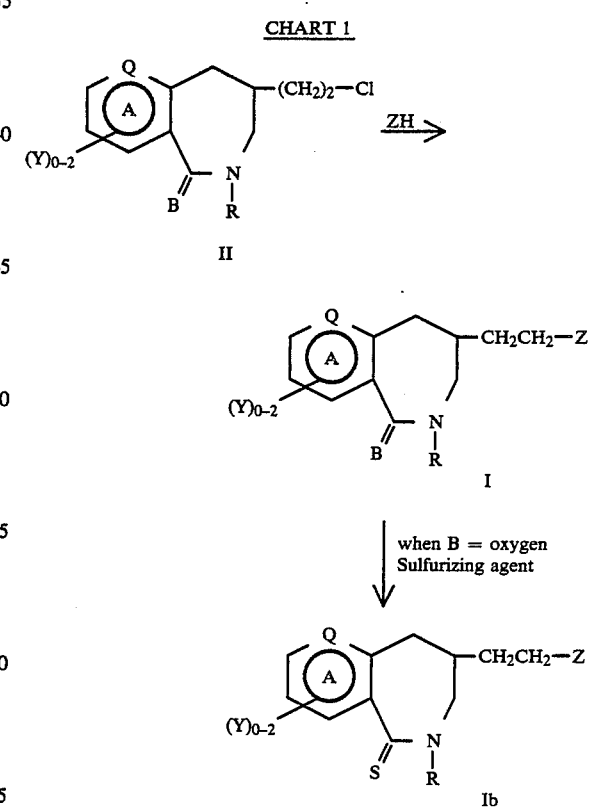

Footnote to Chart I:
A, Y, Z, Q, B and R are defined under Formula I.

CHART 2
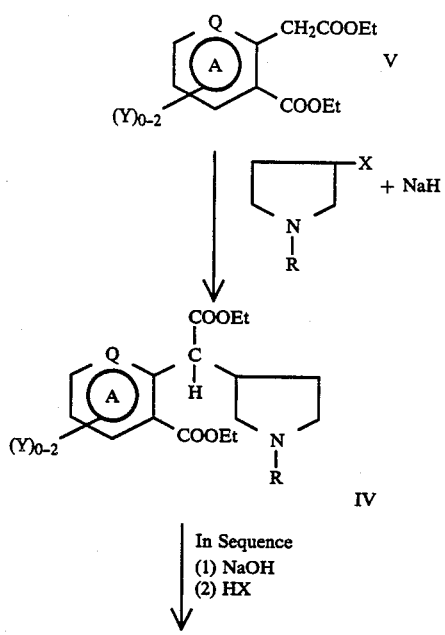
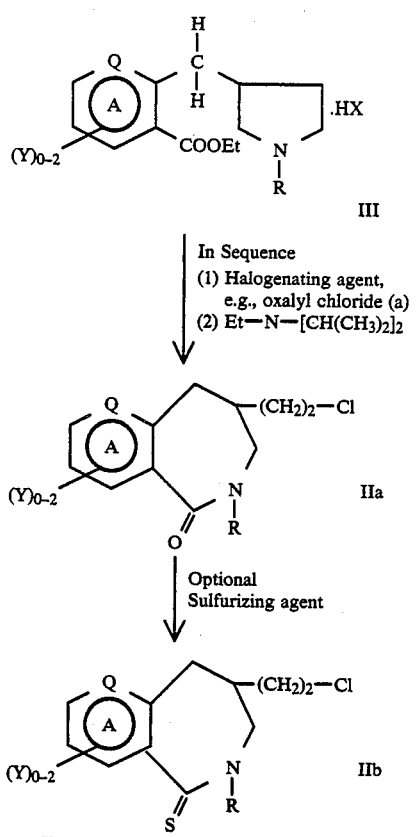
Footnote to Chart 2:
A, Y, Q and R are as defined under Formula I; X = Cl or Br.
(a) Among suitable halogenating agents are oxalyl chloride, triphenylphosphine and carbontetrachloride, phosphorus pentahalides, phosphorus trihalides and triphenylphosphine dihalide.
CHART 3
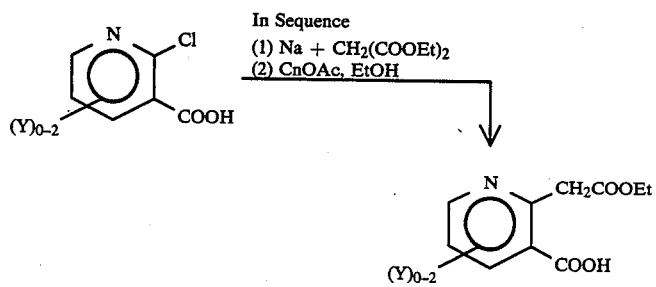

CHART 3

-continued

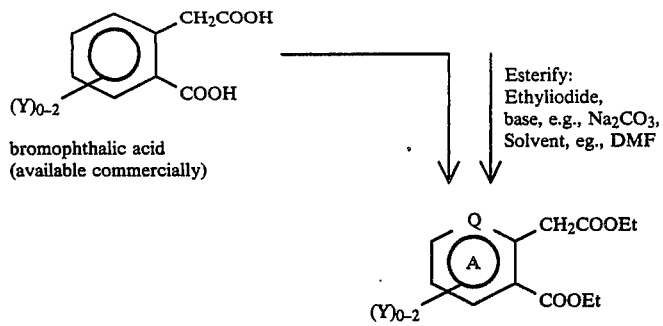

bromophthalic acid
(available commercially)

Esterify:
Ethyliodide,
base, e.g., Na$_2$CO$_3$,
Solvent, eg., DMF

V

Footnote to Chart 3:
Y, Q, and A are as defined under Formula I.

DETAILED DESCRIPTION OF THE INVENTION

The present invention encompasses the novel aromatic tetrahydroazepine derivatives of Formulas I and II and novel compounds of Formulas III and IV all as composition of matter and a process which encompasses preparation of compounds of Formulas I, II, III, and IV.

Chart I illustrates the reaction equations for preparing compounds of Formula I having antihistaminic utility.

Chart II illustrates the reaction equation and sequence for preparing compounds of Formulas II, III, and IV wherein the symbols are as defined under Formula I.

Chart III illustrates the reaction equations for the starting 3-(ethoxycarbonyl)-α-(1-methyl-3-pyrrolidinyl)-2-pyridine acetic acid ethyl ester and the corresponding benzene analog, all of Formula V.

The general preparation of compounds of Formula I, II, III, and IV involves the following sequence of steps wherein the symbols used are as defined above.

Step 1, reacting a compound having the formula:

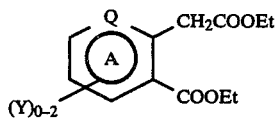

with sodium hydride in suitable solvent, e.g., dimethylsulfoxide followed by a compound having a formula:

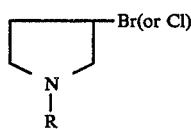

to give a compound having the formula:

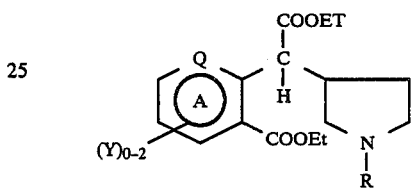

Step 2, reacting a compound prepared in Step 1 with aqueous base and neutralizing with an acid to give a compound having the formula:

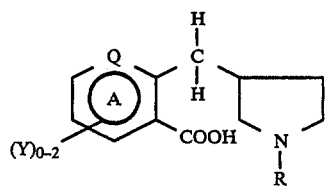

Step 3, halogenating a compound prepared in Step 2 in a suitable solvent such as methylene chloride to give a solution containing a compound having the formula:

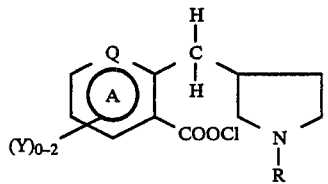

and basifying the solution, preferably with a tertiary amine such as N,N-diisopropylethyl amine and allowing cyclization to occur to give a compound having the formula:

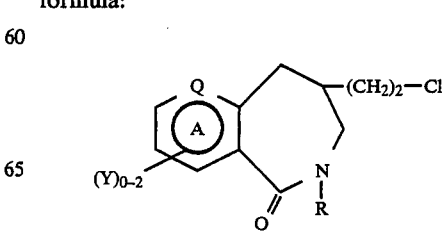

Step 4, optionally sulfurizing the compound prepared in Step 3 with an agent described hereinabove in a suitable solvent as acetonitrile-toluene to give a compound having the formula:

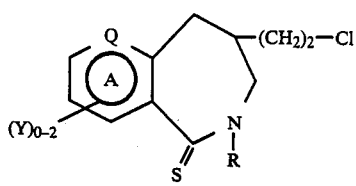

Step 5, reacting the compound prepared in Steps 3 or 4 with an amine having the formula:

ZH wherein Z is as defined under Formula I to give a compound having the formula:

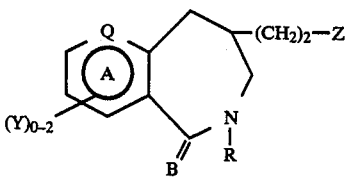

Step 6, optionally sulfurizing a compound prepared in Step 5 wherein B is oxygen to give a compound having the formula:

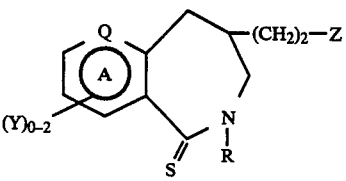

Compounds of Formula I wherein Q is nitrogen are preferred for use as antihistaminics, consequently compounds of Formulas II, III, and IV wherein Q is nitrogen are also preferred for use in synthesis.

The following preparations 1–8 illustrate the synthetic methods used to prepared compounds of Formulas III and IV above. The following intermediates 1–4 illustrate the preparation of compounds of Formula II and the examples illustrate the preparation of compounds of Formula I. The scope of the invention is not limited, however, by these preparations, intermediates, and examples.

PREPARATION 1

3-(Ethoxycarbonyl)-2-pyridineacetic acid ethyl ester

To a mixture of 54 g (0.26 mole) of 3-carboxy-2-pyridineacetic acid ethyl ester* and 24.4 g (0.29 mole) of sodium bicarbonate in 300 ml of dimethylformamide was added 60.8 g (0.39 mole) of ethyliodide. The mixture was stirred at 50° C. for 24 hr; cooled to 25° C. and treated with 300 ml of water. The aqueous solution was extracted 3 times with isopropyl ether. The isopropyl ether solution was extracted with dilute hydrochloric acid. The acid layer was made basic with sodium hydroxide and extracted with isopropyl ether. The ether layer was dried over anhydrous sodium sulfate, concentrated and the residue was distilled to give 47 g (76%), b.p. 128°–130° C./0.5 mm.

*D. E. Amos and W. D. Dodde, J. Chem. Soc. Perkis Trans. 1(5)705-10(1972).

PREPARATION 2

3-(Ethoxycarbonyl)-α-(1-methyl-3-pyrrolidinyl)-2-pyridineacetic acid ethyl ester To a suspension of 8 g (0.2 mole) of 60% sodium hydride/mineral oil in 500 ml of dimethylsulfoxide was added dropwise at room temperature 40 g (0.17 mole) of 3-(ethoxycarbonyl)-2-pyridineacetic acid ethyl ester in 40 ml of dimethylsulfoxide. After stirring a few minutes, 30 g (0.18 mole) of 3-bromo-1-methylprrolidine was added and the solution was stirred at room temperature for 1 hr followed by heating to 60° C. for 7 hr. The resulting solution was extracted 9 times with 200 ml portions of isopropyl ether. The combined isopropyl ether extract was extracted three times with dilute hydrochloric acid. The combined acidic extract was made basic with sodium carbonate and extracted 2 times with isopropyl ether. The last isopropyl ether extracts were combined, dried over anhydrous sodium sulfate and concentrated to give 40 g of oil. The mass spectra and NMR were in agreement with the structure of the title compound.

PREPARATION 3

2-(Methyl-3-pyrrolidinylmethyl)-3-pyridinecarboxylic acid hydrochloride

A solution of 12 g (0.3 mole) of sodium hydroxide in 150 ml of water was added to 37 g of crude oily 3-(ethoxycarbonyl)-α-(1-methyl-3-pyrrolidinyl)-2-pyridineacetic acid ethyl ester obtained in Preparation 2 and the mixture was stirred at 65° C. for 1 hr. The resulting solution was extracted six times with 75 ml portions of chloroform. The aqueous layer was separated and the pH was adjusted to 4 with concentrated hydrochloric acid. The solution was heated to reflux for 1 hr and concentrated on a rotary evaporator. The residue was stirred for 15 minutes in 150 ml of boiling methanol and the mixture was filtered. The filtrate was concentrated on the rotary evaporator. The residue was dissolved in 150 ml of chloroform and the solution was concentrated on the rotary evaporator three times to remove traces of methanol and water. A glassy residue weighing 25 g was obtained. The Infra Red spectra of the residue gave an acid carbonyl peak (1700 cm). The mass spectra (CI) showed a peak for a mass of 320. The 60 MHZ proton NMR spectrum of the product is consistent with the following structure:

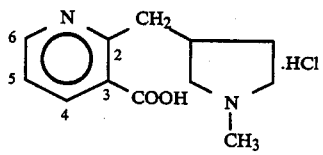

δ: 8.45 (dd, 1H, H-6, J=5.0 Hz, J=2.0 Hz), 8.10 (dd, 1H, H-4, J=10.0 Hz, J=2.0 Hz), 7.35 (s, CHCl$_3$), 7.15 (dd, 1H, H-5, J=5.0 Hz, J=10.0 Hz), 2.95–3.80 (complex m, 7H, 2CH$_2$'s α to N, bridge CH$_2$, 1CH), 2.75 (s, 3H, CH$_3$), 1.70–2.40 (broad m, 2H, CH$_2$β to N).

PREPARATION 4

Homophthalic acid, diethyl ester

Following the esterification and isolation procedures of Preparation 1, and using 2–3 moles of ethyliodide the title compound is obtained starting with homophthalic acid.

Similarly the following are esterified:
(a) 2-carboxy-4-chlorobenzeneacetic acid,
(b) 2-carboxy-4-methylbenzeneacetic acid,
(c) 2-carboxy-5-chlorobenzeneacetic acid,
(d) 2-carboxy-4-nitrobenzeneacetic acid,
(e) 2-carboxy-4-(dimethylamino)-benzeneacetic acid, and
(f) 2-carboxy-4-phenylbenzeneacetic acid to give the following diethyl esters:
(a) 4-chloro-2-(ethoxycarbonyl)-benzeneacetic acid ethyl ester,
(b) 2-(ethoxycarbonyl)-4-methyl-benzeneacetic acid ethyl ester,
(c) 5-chloro-2-(ethoxycarbonyl)-benzeneacetic acid ethyl ester,
(d) 2-(ethoxycarbonyl)-4-nitro-benzene acetic acid ethyl ester,
(e) 4-(dimethylamino)-2-(ethoxycarbonyl)-benzeneacetic acid ethyl ester, and
(f) 2-(ethoxycarbonyl)-4-phenyl-benzeneacetic acid ethyl ester.

PREPARATION 5

Following the esterification procedure of Preparation 1, the following are esterified using with ethyl iodide:
(a) 3-carboxy-5-chloro-2-pyridineacetic acid ethyl ester,
(b) 3-carboxy-5-methyl-2-pyridineacetic acid ethyl ester,
(c) 3-carboxy-6-chloro-2-pyridineacetic acid ethyl ester,
(d) 3-carboxy-5-nitro-2-pyridineacetic acid ethyl ester,
(e) 3-carboxy-5-(dimethylamino)-2-pyridineacetic acid ethyl ester, and
(f) 3-carboxy-5-phenyl-2-pyridineacetic acid ester to give the following diethyl esters:
(a) 5-chloro-3-(ethoxycarbonyl)-2-pyridineacetic acid ethyl ester,
(b) 3-(ethoxycarbonyl)-5-methyl-2-pyridineacetic acid ethyl ester,
(c) 6-chloro-3-(ethoxycarbonyl)-2-pyridineacetic acid ethyl ester,
(d) 3-(ethoxycarbonyl)-5-nitro-2-pyridineacetic acid ethyl ester,
(e) 5-(dimethylamino)-3-(ethoxycarbonyl)-2-pyridineacetic acid ethyl ester, and
(f) 3-(ethoxycarbonyl)-5-phenyl-2-pyridineacetic acid ethyl ester.

PREPARATION 6

Following the procedure of Preparation 2 and substituting the following for 3-(ethoxycarbonyl)-2-pyridineacetic acid ethyl ester:
(a) 4-chloro-2-(ethoxycarbonyl)-benzeneacetic acid ethyl ester,
(b) 2-(ethoxycarbonyl)-4-methyl-benzeneacetic acid ethyl ester,
(c) 5-chloro-2-(ethoxycarbonyl)-benzeneacetic acid ethyl ester,
(d) 2-(ethoxycarbonyl)-4-nitro-benzeneacetic acid ethyl ester,
(e) 4-(dimethylamino)-2-(ethoxycarbonyl)-benzeneacetic acid ethyl ester,
(f) 2-(ethoxycarbonyl)-4-phenyl-benzeneacetic acid ethyl ester,
(g) 5-chloro-3-(ethoxycarbonyl)-2-pyridineacetic acid ethyl ester,
(h) 3-(ethoxycarbonyl)-5-methyl-2-pyridineacetic acid ethyl ester,
(i) 6-chloro-3-(ethoxycarbonyl)-2-pyridineacetic acid ethyl ester,
(j) 3-(ethoxycarbonyl)-5-nitro-2-pyridineacetic acid ethyl ester,
(k) 5-(dimethylamino)-3-(ethoxycarbonyl)-2-pyridineacetic acid ethyl ester, and
(l) 3-(ethoxycarbonyl)-5-phenyl-2-pyridineacetic acid ethyl ester there are obtained the following:
(a) 4-chloro-2-(ethoxycarbonyl)-α-(1-methyl-3-pyrrolidinyl)-benzeneacetic acid ethyl ester,
(b) 2-(ethoxycarbonyl)-4-methyl-α-(1-methyl-3-pyrrolidinyl)-benzeneacetic acid ethyl ester,
(c) 5-chloro-2-(ethoxycarbonyl)-α-(1-methyl-3-pyrrolidinyl)-benzeneacetic acid ethyl ester,
(d) 2-(ethoxycarbonyl)-4-nitro-α-(1-methyl-3-pyrrolidinyl)-benzeneacetic acid ethyl ester,
(e) 4-(dimethylamino)-2-(ethoxycarbonyl)-α-(1-methyl-3-pyrrolidinyl)-benzeneacetic acid ethyl ester,
(f) 2-(ethoxycarbonyl)-4-phenyl-α-(1-methyl-3-pyrrolidinyl)-2-pyridineacetic acid ethyl ester,
(g) 5-chloro-3-(ethoxycarbonyl)-α-(1-methyl-3-pyrrolidinyl)-2-pyridineacetic acid ethyl ester,
(h) 3-(ethoxycarbonyl)-5-methyl-α-(1-methyl-3-pyrrolidinyl)-2-pyridineacetic acid ethyl ester,
(i) 6-chloro-3-(ethoxycarbonyl)-α-(1-methyl-3-pyrrolidinyl)-2-pyridineacetic acid ethyl ester,
(j) 3-(ethoxycarbonyl)-5-nitro-α-(1-methyl-3-pyrrolidinyl)-2-pyridineacetic acid ethyl ester,
(k) 5-(dimethylamino)-3-(ethoxycarbonyl)-α-(1-methyl-3-pyrrolidinyl)-2-pyridineacetic acid ethyl ester, and
(l) 3-(ethoxycarbonyl)-5-phenyl-α-(1-methyl-3-pyrrolidinyl)-2-pyridineacetic acid ethyl ester.

PREPARATION 7

Following the procedure of Preparation 2 and substituting the following for 3-bromo-1-methylpyrrolidine:
(a) 3-bromo-1-ethylpyrrolidine,
(b) 3-bromo-1-cyclohexylpyrrolidine,
(c) 3-bromo-1-benzylpyrrolidine,
(d) 3-bromo-1-(4-chlorophenyl)methylpyrrolidine, and
(e) 3-bromo-1-(2-methoxyphenyl)methylpyrrolidine there are obtained
(a) 3-(ethoxycarbonyl)-α-(1-ethyl-3-pyrrolidinyl)-2-pyridineacetic acid ethyl ester,
(b) 3-(ethoxycarbonyl)-α-(1-cyclohexyl-3-pyrrolidinyl)-2-pyridineacetic acid ethyl ester,
(c) 3-(ethoxycarbonyl)-α-(1-phenylmethyl-3-pyrrolidinyl)-2-pyridineacetic acid ethyl ester,
(d) 3-(ethoxycarbonyl)-α-[1-(4-chlorophenylmethyl)-3-pyrrolidinyl]-2-pyridineacetic acid ethyl ester, and
(e) 3-(ethoxycarbonyl)-α-[1-(2-methoxyphenylmethyl)-3-pyrrolidinyl]-2-pyridineacetic acid ethyl ester.

PREPARATION 8

Following the procedure of preparation 3 and substituting the following for 3-(ethoxycarbonyl)-α-(1-methyl-3-pyrrolidinyl)-2-pyridineacetic acid ethyl ester:
(a) 4-chloro-2-(ethoxycarbonyl)-α-(1-methyl-3-pyrrolidinyl)-benzeneacetic acid ethyl ester, (b) 2-(ethoxycarbonyl)-4-methyl-α-(1-methyl-3-pyrrolidinyl)-benzeneacetic acid ethyl ester,
(c) 5-chloro-2-(ethoxycarbonyl)-α-(1-methyl-3-pyrrolidinyl)-benzeneacetic acid ethyl ester,
(d) 2-(ethoxycarbonyl)-4-nitro-α-(1-methyl-3-pyrrolidinyl)-benzeneacetic acid ethyl ester,
(e) 4-(dimethylamino)-2-(ethoxycarbonyl)-α-(1-methyl-3-pyrrolidinyl)-benzeneacetic acid ethyl ester,
(f) 2-(ethoxycarbonyl)-4-phenyl-α-(1-methyl-3-pyrrolidinyl)-benzeneacetic acid ethyl ester,
(g) 5-chloro-3-(ethoxycarbonyl)-α-(1-methyl-3-pyrrolidinyl)-2-pyridineacetic acid ethyl ester,
(h) 3-(ethoxycarbonyl)-5-methyl-α-(1-methyl-3-pyrrolidinyl)-2-pyridineacetic acid ethyl ester,
(i) 6-chloro-3-(ethoxycarbonyl)-α-(1-methyl-3-pyrrolidinyl)-2-pyridineacetic acid ethyl ester,
(j) 3-(ethoxycarbonyl)-5-nitro-α-(1-methyl-3-pyrrolidinyl)-2-pyridineacetic acid ethyl ester,
(k) 5-(dimethylamino)-3-(ethoxycarbonyl)-α-(1-methyl-3-pyrrolidinyl)-2-pyridineacetic acid ethyl ester,
(l) 3-(ethoxycarbonyl)-5-phenyl-α-(1-methyl-3-pyrrolidinyl)-2-pyridineacetic acid ethyl ester,
(m) 3-(ethoxycarbonyl)-α-(1-ethyl-3-pyrrolidinyl)-2-pyridineacetic acid ethyl ester,
(n) 3-(ethoxycarbonyl)-α-(1-cyclohexyl-3-pyrrolidinyl)-2-pyridineacetic acid ethyl ester,
(o) 3-(ethoxycarbonyl)-α-(1-phenylmethyl-3-pyrrolidinyl)-2-pyridineacetic acid ethyl ester,
(p) 3-(ethoxycarbonyl)-α-[1-(4-chlorophenylmethyl)-3-pyrrolidinyl]-2-pyridineacetic acid ethyl ester, and
(q) 3-(ethoxycarbonyl)-α-[1-(2-methoxyphenylmethyl)-3-pyrrolidinyl]-2-pyridineacetic acid ethyl ester
there are obtained:
(a) 5-chloro-2-(1-methyl-3-pyrrolidinylmethyl)benzoic acid hydrochloride,
(b) 5-methyl-2-(1-methyl-3-pyrrolidinylmethyl)benzoic acid hydrochloride,
(c) 4-chloro-2-(1-methyl-3-pyrrolidinylmethyl)benzoic acid hydrochloride,
(d) 5-nitro-2-(1-methyl-3-pyrrolidinylmethyl)benzoic acid hydrochloride,
(e) 5-(dimethylamino)-2-(1-methyl-3-pyrrolidinylmethyl)benzoic acid hydrochloride,
(f) 5-phenyl-2-(1-methyl-3-pyrrolidinylmethyl)benzoic acid hydrochloride,
(g) 5-chloro-2-(1-methyl-3-pyrrolidinylmethyl)-3-pyridinecarboxylic acid hydrochloride,
(h) 5-methyl-2-(1-methyl-3-pyrrolidinylmethyl)-3-pyridinecarboxylic acid hydrochloride,
(i) 6-chloro-2-(1-methyl-3-pyrrolidinylmethyl)-3-pyridinecarboxylic acid hydrochloride,
(j) 5-nitro-2-(1-methyl-3-pyrrolidinylmethyl)-3-pyridinecarboxylic acid hydrochloride,
(k) 5-(dimethylamino)-2-(1-methyl-3-pyrrolidinylmethyl)-3-pyridinecarboxylic acid hydrochloride,
(l) 5-phenyl-2-(1-methyl-3-pyrrolidinylmethyl)-3-pyridinecarboxylic acid hydrochloride,
(m) 2-(1-ethyl-3-pyrrolidinylmethyl)-3-pyridinecarboxylic acid hydrochloride,
(n) 2-(1-cyclohexyl-3-pyrrolidinylmethyl)-3-pyridinecarboxylic acid hydrochloride,
(o) 2-(1-phenylmethyl-3-pyrrolidinylmethyl)-3-pyridinecarboxylic acid hydrochloride,
(p) 2-[1-(4-chlorophenyl)methyl-3-pyrrolidinylmethyl]-3-pyridinecarboxylic acid hydrochloride, and
(q) 2-[1-(2-methoxyphenyl)methyl-3-pyrrolidinylmethyl]-3-pyridinecarboxylic acid hydrochloride.

INTERMEDIATE 1

8-(2-Chloroethyl)-6,7,8,9-tetrahydro-6-methyl-5H-pyrido[3,2-c]azepin-5-one hydrochloride[1:1]

To a solution of 24 g (0.094 mole) of 2-(1-methyl-3-pyrrolidinylmethyl)-3-pyridinecarboxylic acid hydrochloride (the product of Preparation 3) in 200 ml of methylene chloride was added, dropwise, 18 g (0.14 mole) of oxalyl chloride. The resulting mixture was stirred at room temperature for 1.5 hr to give a solution to which was added, dropwise, 36 g (0.28 mole) of N,N-diisopropylethylamine while cooling to 20°-30° C. The mixture was stirred for two hr and then extracted with dilute aqueous sodium hydroxide. The aqueous sodium hydroxide layer (solution) was back extracted three times with methylene chloride. The combined methylene chloride extracts were dried over anhydrous sodium sulfate and concentrated on a rotary evaporator. The residue was chromatographed on a Waters ® 500 HPLC using a silica column and eluting with ethyl acetate and evaporating the eluant to give 7.0 g of the free base of the title compound. Part of the free base was converted to the hydrochloride salt with hydrogen chloride in isopropyl alcohol, m.p. 199°-202° C.

Analysis: Calculated $C_{12}H_{16}N_2OCl_2$: C, 52.38; H, 5.86; N, 10.18. Found: C, 52.57; H, 5.90; N, 10.17.

INTERMEDIATE 2

8-(2-Chloroethyl)-6,7,8,9-tetrahydro-6-methyl-5H-pyrido[3,2-c]azepin-5-thione

To a solution of 4.7 g (0.02 mole) of 8-(2-chloroethyl)-6,7,8,9-tetrahydro-6-methyl-5H-pyrido[3,2-c]azepin-5-one hydrochloride[1:1] in 50 ml of acetonitrile was added 4.7 g (0.02 mole) of phosphorus pentasulfide. The mixture was stirred at reflux for 2.5 hr, cooled and treated with 50 ml of toluene. The toluene was decanted from the yellow residue (original residue). The toluene was extracted with sodium bicarbonate, dried and concentrated leaving a residue of 1.2 g of yellow solid. The original residue was partitioned between chloroform and dilute aqueous sodium hydroxide. The chloroform layer was dried over anhydrous sodium sulfate and concentrated to give a residue which was shown by TLC (silica, ethyl acetate) to the same as the 1.2 g yellow solid collected above. The solids were combined and chromatographed on a Waters ® 500 HPLC using a silica column and eluting with 25% ethyl acetate-75% isopropyl ether to give 2.6 g (51%) of solids, m.p. 110°-120° C.

Analysis: Calculated $C_{12}H_{15}N_2OCl$: C, 56.57; H, 5.93; N, 10.99. Found: C, 57.30; H, 6.07; N, 10.04.

INTERMEDIATE 3

4-(2-Chloroethyl)-2,3,4,5-tetrahydro-2-methyl-1H-2-benzazepin-1-one hydrochloride Following the procedure of Intermediate 1, and substituting 2-(1-methyl-3-pyrrolidinylmethyl)benzenecarboxylic acid for 2-(1-methyl-3-pyrrolidinylmethyl)-3-pyridinecarboxylic acid, the title compound is obtained.

INTERMEDIATE 4

Following the procedure of Intermediate 1, and substituting the following for 2-(1-methyl-3-pyrrolidinylmethyl)-3-pyridinecarboxylic acid hydrochloride:
(a) 5-chloro-2-(1-methyl-3-pyrrolidinylmethyl)benzoic acid hydrochloride, (b) 5-methyl-2-(1-methyl-3-pyrrolidinylmethyl)benzoic acid hydrochloride,
(c) 4-chloro-2-(1-methyl-3-pyrrolidinylmethyl)benzoic acid hydrochloride,
(d) 5-nitro-2-(1-methyl-3-pyrrolidinylmethyl)benzoic acid hydrochloride,
(e) 5-(dimethylamino)-2-(1-methyl-3-pyrrolidinylmethyl)benzoic acid hydrochloride,
(f) 5-phenyl-2-(1-methyl-3-pyrrolidinylmethyl)benzoic acid hydrochloride,
(g) 5-chloro-2-(1-methyl-3-pyrrolidinylmethyl)-3-pyridinecarboxylic acid hydrochloride,
(h) 5-methyl-2-(1-methyl-3-pyrrolidinylmethyl)-3-pyridinecarboxylic acid hydrochloride,
(i) 6-chloro-2-(1-methyl-3-pyrrolidinylmethyl)-3-pyridinecarboxylic acid hydrochloride,
(j) 5-nitro-2-(1-methyl-3-pyrrolidinylmethyl)-3-pyridinecarboxylic acid hydrochloride,
(k) 5-(dimethylamino)-2-(1-methyl-3-pyrrolidinylmethyl)-3-pyridinecarboxylic acid hydrochloride,
(l) 5-phenyl-2-(1-methyl-3-pyrrolidinylmethyl)-3-pyridinecarboxylic acid hydrochloride,
(m) 2-(1-ethyl-3-pyrrolidinylmethyl)-3-pyridinecarboxylic acid hydrochloride,
(n) 2-(1-cyclohexyl-3-pyrrolidinylmethyl)-3-pyridinecarboxylic acid hydrochloride,
(o) 2-(1-phenylmethyl-3-pyrrolidinylmethyl)-3-pyridinecarboxylic acid hydrochloride,
(p) 2-[1-(4-chlorophenyl)methyl-3-pyrrolidinylmethyl]-3-pyridinecarboxylic acid hydrochloride, and
(q) 2-[1-(2-methoxyphenyl)methyl-3-pyrrolidinylmethyl]-3-pyridinecarboxylic acid hydrochloride
there are obtained the following:
(a) 8-chloro-4-(2-chloroethyl)-2,3,4,5-tetrahydro-2-methyl-1H-2-benzazepin-1-one hydrochloride,
(b) 4-(2-chloroethyl)-8-methyl-2,3,4,5-tetrahydro-2-methyl-1H-2-benzazepin-1-one hydrochloride,
(c) 7-chloro-4-(2-chloroethyl)-2,3,4,5-tetrahydro-2-methyl-1H-2-benzazepin-1-one hydrochloride,
(d) 4-(2-chloroethyl)-8-nitro-2,3,4,5-tetrahydro-2-methyl-1H-2-benzazepin-1-one hydrochloride,
(e) 4-(2-chloroethyl)-8-(dimethylamino)-2,3,4,5-tetrahydro-2-methyl-1H-2-benzazepin-1-one hydrochloride,
(f) 4-(2-chloroethyl)-8-phenyl-2,3,4,5-tetrahydro-2-methyl-1H-2-benzazepin-1-one hydrochloride,
(g) 3-chloro-8-(2-chloroethyl)-6,7,8,9-tetrahydro-6-methyl-5H-pyrido[3,2-c]azepin-5-one hydrochloride,
(h) 8-(2-chloroethyl)-3-methyl-6,7,8,8-tetrahydro-6-methyl-5H-pyrido[3,2-c]azepin-5-one hydrochloride,
(i) 2-chloro-8-(2-chloroethyl)-6,7,8,9-tetrahydro-6-methyl-5H-pyrido[3,2-c]azepin-5-one hydrochloride,
(j) 8-(2-chloroethyl)-3-nitro-6,7,8,9-tetrahydro-6-methyl-5H-pyrido[3,2-c]azepin-5-one hydrochloride,
(k) 8-(2-chloroethyl)-3-(dimethylamino)-6,7,8,9-tetrahydro-6-methyl-5H-pyrido[3,2-c]azepin-5-one hydrochloride,
(l) 8-(2-chloroethyl)-3-phenyl-6,7,8,9-tetrahydro-6-methyl-5H-pyrido[3,2-c]azepin-5-one hydrochloride,
(m) 8-(2-chloroethyl)-6,7,8,9-tetrahydro-6-ethyl-5H-pyrido[3,2-c]azepin-5-one hydrochloride,
(n) 8-(2-chloroethyl)-6,7,8,9-tetrahydro-6-cyclohexyl-5H-pyrido[3,2-c]azepin-5-one hydrochloride,
(o) 8-(2-chloroethyl)-6,7,8,9-tetrahydro-6-phenylmethyl-5H-pyrido[3,2-c]azepin-5-one hydrochloride,
(p) 8-(2-chloroethyl)-6,7,8,9-tetrahydro-6-(4-chlorophenylmethyl)-5H-pyrido[3,2-c]azepin-5-one hydrochloride, and
(q) 8-(2-chloroethyl)-6,7,8,9-tetrahydro-6-(2-methoxyphenylmethyl)-5H-pyrido[3,2-c]azepin-5-one hydrochloride.

TABLE 1

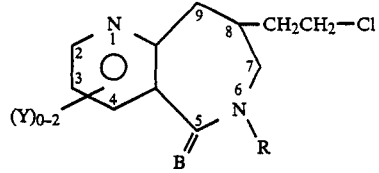

| Intermediate No. | Y | B | R | Salt |
|---|---|---|---|---|
| 1 | — | O | —CH$_3$ | HCl |
| 2 | — | S | —CH$_3$ | — |
| 4g | 3-Cl | O | —CH$_3$ | HCl |
| 4h | 3-CH$_3$ | O | —CH$_3$ | HCl |
| 4i | 2-Cl | O | —CH$_3$ | HCl |
| 4j | 3-NO$_2$ | O | —CH$_3$ | HCl |
| 4k | 3-N(CH$_3$)$_2$ | O | —CH$_3$ | HCl |
| 4l | 3-C$_6$H$_5$ | O | —CH$_3$ | HCl |
| 4m | — | O | —C$_2$H$_5$ | HCl |
| 4n | — | O | —C$_6$H$_{11}$ | HCl |
| 4o | — | O | —CH$_2$C$_6$H$_5$ | HCl |
| 4p | — | O | 4-Cl-C$_6$H$_4$—CH$_2$— | HCl |
| 4q | — | O | 2-(OCH$_3$)—C$_6$H$_4$CH$_2$— | HCl |

TABLE 2

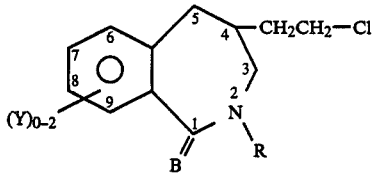

| Intermediate No. | Y | B | R | Salt |
|---|---|---|---|---|
| 3 | — | O | —CH$_3$ | HCl |
| 4a | 8-Cl | O | —CH$_3$ | HCl |
| 4b | 8-CH$_3$ | O | —CH$_3$ | HCl |
| 4c | 7-Cl | O | —CH$_3$ | HCl |
| 4d | 8-NO$_2$ | O | —CH$_3$ | HCl |
| 4e | 8-N(CH$_3$)$_2$ | O | —CH$_3$ | HCl |
| 4f | 8-C$_6$H$_5$ | O | —CH$_3$ | HCl |

EXAMPLE 1

8-[2-(Dimethylamino)ethyl]-6,7,8,9-tetrahydro-6-methyl-5H-pyrido[3,2-c]azepin-5-one fumarate[1:2]

To 20 ml of dimethylamine was added 2.0 g (0.0073 mole) of 8-(2-chloroethyl)-6,7,8,9-tetrahydro-6-methyl-5H-pyrido[3,2-c]azepin-5-one and the solution was stirred in a sealed flask at room temperature for 96 hr. The excess dimethylamine was allowed to evaporate and the residue was partitioned between chloroform and aqueous potassium carbonate. The aqueous layer was extracted twice with chloroform. The combined chloroform extract was dried over anhydrous sodium sulfate and concentrated. The residue containing the free base of the title compound was dissolved in 20 ml of hot isopropyl alcohol and the solution was treated with 1.0 g of fumaric acid. Isopropyl ether, 20 ml was added to give 1.8 g (51%) of crystals, m.p. 149°–151° C.

Analysis: Calc'd for C$_{22}$H$_{29}$N$_3$O$_9$: C, 55.11; H, 6.10; N, 8.76. Found: C, 54.99; H, 6.24; N, 8.97.

EXAMPLE 2

8-[2-(Dimethylamino)ethyl]-6,7,8,9-tetrahydro-6-methyl-5H-pyrido[3,2-c]azepin-5-thione fumarate[1:1]

To 20 ml of dimethylamine was added 2.4 g of 8-(2-chloroethyl)-6,7,8,9-tetrahydro-6-methyl-5H-pyrido[3,2-c]azepin-5-thione and the solution was stirred in a sealed flask at room temperature for 48 hr. The excess dimethylamine was allowed to evaporate and the residue was partitioned between chloroform and dilute sodium hydroxide. The aqueous layer was extracted 2 times with chloroform. The combined chloroform extract was dried over anhydrous sodium sulfate and concentrated. The residue was dissolved in 20 ml of hot isopropyl alcohol and the solution was treated with 1.4 g of fumaric acid. Isopropyl ether, 20 ml was added to give 2.7 g (76%), m.p. 150°–153° C.

Analysis: Calc'd for $C_{18}H_{25}N_3O_4S$: C, 56.97; H, 6.64; N, 11.07. Found: C, 56.56; H, 6.68; N, 10.77.

EXAMPLE 3

Following the procedure of Example 1 and substituting the following for 8-(2-chloroethyl)-6,7,8,9-tetrahydro-6-methyl-5H-pyrido[3,2-c]azepin-5-one:
(a) 3-chloro-8-(2-chloroethyl)-6,7,8,9-tetrahydro-6-methyl-5H-pyrido-[3,2-c]azepin-5-one,
(b) 8-(2-chloroethyl)-3-methyl-6,7,8,9-tetrahydro-6-methyl-5H-pyrido[3,2-c]azepin-5-one,
(c) 2-chloro-8-(2-chloroethyl)-6,7,8,9-tetrahydro-6-methyl-5H-pyrido-[3,2-c]azepin-5-one,
(d) 8-(2-chloroethyl)-3-nitro-6,7,8,9-tetrahydro-6-methyl-5H-pyrido[3,2-c]azepin-5-one,
(e) 8-(2-chloroethyl)-3-(dimethylamino)-6,7,8,9-tetrahydro-6-methyl-5H-pyrido[3,2-c]azepin-5-one,
(f) 8-(2-chloroethyl)-3-phenyl-6,7,8,9-tetrahydro-6-methyl-5H-pyrido[3,2-c]azepin-5-one,
(g) 8-(2-chloroethyl)-6,7,8,9-tetrahydro-6-ethyl-5H-pyrido[3,2-c]azepin-5-one,
(h) 8-(2-chloroethyl)-6,7,8,9-tetrahydro-6-cyclohexyl-5H-pyrido[3,2-c]azepin-5-one,
(i) 8-(2-chloroethyl)-6,7,8,9-tetrahydro-6-phenylmethyl-5H-pyrido[3,2-c]azepin-5-one,
(j) 8-(2-chloroethyl)-6,7,8,9-tetrahydro-6-(4-chlorophenylmethyl)-5H-pyrido[3,2-c]azepin-5-one, and
(k) 8-(2-chloroethyl)-6,7,8,9-tetrahydro-6-(2-methoxyphenylmethyl)-5H-pyrido[3,2-c]azepin-5-one
there are obtained:
(a) 3-chloro-8-[2-(dimethylamino)ethyl]-6,7,8,9-tetrahydro-6-methyl-5H-pyrido[3,2-c]azepin-5-one fumarate,
(b) 8-[2-(dimethylamino)ethyl]-3-methyl-6,7,8,9-tetrahydro-6-methyl-5H-pyrido[3,2-c]azepin-5-one fumarate,
(c) 2-chloro-8-[2-(dimethylamino)ethyl]-6,7,8,9-tetrahydro-6-methyl-5H-pyrido[3,2-c]azepin-5-one fumarate,
(d) 8-[2-(dimethylamino)ethyl]-3-nitro-6,7,8,9-tetrahydro-6-methyl-5H-pyrido[3,2-c]azepin-5-one fumarate,
(e) 3-(dimethylamino)-8-[2-(dimethylamino)ethyl]-6,7,8,9-tetrahydro-6-methyl-5H-pyrido[3,2-c]azepin-5-one fumarate,
(f) 8-[2-(dimethylamino)ethyl]-3-phenyl-6,7,8,9-tetrahydro-6-methyl-5H-pyrido[3,2-c]azepin-5-one fumarate,
(g) 8-[2-(dimethylamino)ethyl]-6,7,8,9-tetrahydro-6-ethyl-5H-pyrido-[3,2-c]azepin-5-one fumarate,
(h) 6-cyclohexyl-8-[2-(dimethylamino)ethyl]-6,7,8,9-tetrahydro-5H-pyrido[3,2-c]azepin-5-one fumarate,
(i) 8-[2-(dimethylamino)ethyl]-6-phenylmethyl-6,7,8,9-tetrahydro-5H-pyrido-[3,2-c]azepin-5-one fumarate,
(j) 6-(4-chlorophenylmethyl)-8-[2-(dimethylamino)ethyl]-6,7,8,9-tetrahydro-5H-pyrido[3,2-c]azepin-5-one fumarate, and
(k) 8-[2-(dimethylamino)ethyl]-6,7,8,9-tetrahydro-6-(2-methoxyphenylmethyl)-5H-pyrido[3,2-c]azepin-5-one.

EXAMPLE 4

Following the procedure of Example 1 and substituting the following for 8-(2-chloroethyl)-6,7,8,9-tetrahydro-6-methyl-5H-pyrido[3,2-c]azepin-5-one:
(a) 4-(2-chloroethyl)-2,3,4,5-tetrahydro-2-methyl-1H-2-benzazepin-1-one,
(b) 8-chloro-4-(2-chloroethyl)-2,3,4,5-tetrahydro-2-methyl-1H-2-benzazepin-1-one,
(c) 4-(2-chloroethyl)-8-methyl-2,3,4,5-tetrahydro-2-methyl-1H-2-benzazepin-1-one,
(d) 7-chloro-4-(2-chloroethyl)-2,3,4,5-tetrahydro-2-methyl-1H-2-benzazepin-1-one,
(e) 4-(2-chloroethyl)-8-nitro-2,3,4,5-tetrahydro-2-methyl-1H-2-benzazepin-1-one,
(f) 4-(2-chloroethyl)-8-(dimethylamino)-2,3,4,5-tetrahydro-2-methyl-1H-2-benzazepin-1-one, and
(g) 4-(2-chloroethyl)-8-phenyl-2,3,4,5-tetrahydro-2-methyl-1H-2-benzazepin-1-one
there are obtained:
(a) 4-[2-(dimethylamino)ethyl-2,3,4,5-tetrahydro-2-methyl-1H-2-benzazepin-1-one fumarate,
(b) 8-chloro-4-[2-(dimethylamino)ethyl]-2,3,4,5-tetrahydro-2-methyl-1H-2-benzazepin-1-one fumarate,
(c) 4-[2-(dimethylamino)ethyl]-8-methyl-2,3,4,5-tetrahydro-2-methyl-1H-2-benzazepin-1-one fumarate,
(d) 7-chloro-4-[2-(dimethylamino)ethyl]-2,3,4,5-tetrahydro-2-methyl-1H-2-benzazepin-1-one fumarate,
(e) 4-[2-(dimethylamino)ethyl]-8-nitro-2,3,4,5-tetrahydro-2-methyl-1H-2-benzazepin-1-one fumarate,
(f) 4-[2-(dimethylamino)ethyl]-8-(dimethylamino)-2,3,4,5-tetrahydro-2-methyl-1H-2-benzazepin-1-one fumarate, and
(g) 4-[2-(dimethylamino)ethyl]-8-phenyl-2,3,4,5-tetrahydro-2-methyl-1H-2-benzazepin-1-one fumarate.

EXAMPLE 5

8-[2-(Methylamino)ethyl]-6,7,8,9-tetrahydro-6-methyl-5H-pyrido[3,2-c]azepin-5-one fumarate[1:2]

8-(2-Chloroethyl)-6,7,8,9-tetrahydro-6-methyl-5H-pyrido[3,2-c]azepin-5-one in a solution of monomethylamine and ethanol is heated in a steel bomb at abojut 100° C. and the free base of the title compound is recovered as in the procedure of Example 1. The free base of the title compound is reacted with fumaric acid to give the title compound.

EXAMPLE 6

8-[2-(4-Morpholino)ethyl]-6,7,8,9-tetrahydro-6-methyl-5H-pyrido[3,2-c]azepin-5-one fumarate A solution of 8-(2-chloroethyl)-6,7,8,9-tetrahydro-6-methyl-5H-pyrido[3,2-c]azepin-5-one in excess morpholine is refluxed for several hours and then concentrated in vacuo and the resulting free base is isolated and reacted with fumaric acid in isopropyl alcohol to give the title compound.

EXAMPLE 7

8-[2-[(4-Hydroxy-4-phenyl)-1-piperidinyl]ethyl]-6,7,8,9-tetrahydro-6-methyl-5H-pyrido[3,2-c]azepin-5-one hydrochloride A suspension of potassium carbonate, 4-hydroxy-4-phenyl-piperidine and 8-(2-chloroethyl)-6,7,8,9-tetrahydro-6-methyl-5H-pyrido[3,2-c]azepin-5-one in n-butanol is refluxed for several hours. The mixture is filtered and the filtrate is concentrated in vacuo. The residue containing the free base of the title compound is dissolved in a suitable solvent such as ethanol-ligroin and reacted with hydrogen chloride and the title compound is recrystallized from a suitable solvent such as isopropyl alcohol.

EXAMPLE 8

8-[2-[1-(4-Phenyl-1,2,3,6-tetrahydro)pyridinyl]ethyl]-6,7,8,9-tetrahydro-6-methyl-5H-pyrido[3,2-c]azepin-5-one A suspension of 8-(2-chloroethyl)-6,7,8,9-tetrahydro-6-methyl-5H-pyrido[3,2-c]azepin-5-one and potassium carbonate in n-butanol is refluxed for 72 hr. The reaction mixture is filtered hot and the filtrate is cooled to room temperature and refiltered. The last filtrate is concentrated and the residue is recrystallized from a suitable solvent such as ethyl acetate to give the title compound.

EXAMPLE 9

8-[2-(1-Pyrrolidinyl)ethyl]-6,7,8,9-tetrahydro-6-methyl-5H-pyrido[3,2-c]azepin-5-one fumarate 8-(2-Chloroethyl)-6,7,8,9-tetrahydro-6-methyl-5H-pyrido[3,2-c]azepin-5-one hydrochloride is dissolved in excess pyrrolidine. The solution is heated to about 80° C. for several hours and aqueous sodium hydroxide solution is added. The resulting solution is extracted with a suitable solvent such as chloroform and the chloroform extract is concentrated in vacuo. The residue is dissolved in a suitable solvent such as isopropyl alcohol and reacted with fumaric acid to give a precipitate of the title compound.

EXAMPLE 10

8-[2-(Dibutylamino)ethyl]-6,7,8,9-tetrahydro-6-methyl-5H-pyrido[3,2-c]azepin-5-one oxalate A solution of 8-(2-chloroethyl)-6,7,8,9-tetrahydro-6-methyl-5H-pyrido[3,2-c]azepin-5-one hydrochloride in a solution of di-n-butylamine and dimethylformamide is stirred at about 100° C. for several hours. The solution is cooled and basified with dilute aqueous sodium hydroxide solution. The mixture is extracted with a suitable solvent such as chloroform and the chloroform extract is concentrated and the concentrate subjected to low vacuum to remove dimethylformamide and butanol. The residue, the free base of the title compound is converted to the title compound by reacting with oxalic acid in a suitable solvent such as isopropyl alcohol.

EXAMPLE 11

8-[2-(1-Piperidinyl)ethyl]-6,7,8,9-tetrahydro-6-methyl-5H-pyrido[3,2-c]azepin-5-one oxalate A solution of 8-(2-chloroethyl)-6,7,8,9-tetrahydro-6-methyl-5H-pyrido[3,2-c]azepin-5-one hydrochloride in an excess of piperidine is heated to about 80° C. for about 0.5 hr. Unreacted piperidine is removed on a rotary evaporator and the residue containing the free base of the title compound is taken up in chloroform and the chloroform layer is washed with dilute aqueous sodium hydroxide and concentrated. Reaction with oxalic acid in a suitable solvent such as isopropyl alcohol gives the title compound.

EXAMPLE 12

8-[2-[(Methyl)(phenylmethyl)amino]ethyl]-6,7,8,9-tetrahydro-6-methyl-5H-pyrido[3,2-c]-azepin-5-one maleate A solution of 8-(2-chloroethyl)-6,7,8,9-tetrahydro-6-methyl-5H-pyrido[3,2-c]azepin-5-one hydrochloride in excess (methyl)(benzyl)amine is heated to about 80° C. for several hours. The unreacted amine is removed under reduced pressure and the residue is taken up in chloroform and the solution washed with dilute aqueous base. The chloroform layer is concentrated to give the free base of the title compound which is reated with maleic acid in hot isopropyl alcohol. The title compound is obtained upon cooling of the solution.

EXAMPLE 13

8-[2-[(Methyl)(phenyl)amino]ethyl]-6,7,8,9-tetrahydro-6-methyl-5H-pyrido[3,2-c]azepin-5-one A solution of 8-(2-chloroethyl)-6,7,8,9-tetrahydro-6-methyl-5H-pyrido[3,2-c]azepin-5-one hydrochloride in excess N-methylaniline is heated to about 95° C. for 2 days. Excess N-methylaniline is removed at reduced pressure and the residue is taken up in chloroform. The chloroform layer is washed with dilute aqeuous base, decolorized with activated carbon and dried over sodium sulfate, filtered and concentrated. The residue is dissolved in a suitable solvent and purified by high pressure liquid chromatography using a silica gel column and ethyl acetate. The product is recrystallized from ethyl acetate.

EXAMPLE 14

8-[2-(2,5-Dimethyl-1-pyrrolidinyl)ethyl]-6,7,8,9-tetrahydro-6-methyl-5H-pyrido[3,2-c]azepin-5-one fumarate To a solution of 8-(2-chloroethyl)-6,7,8,9-tetrahydro-6-methyl-5H-pyrido[3,2-c]azepin-5-one in absolute ethanol was added 2,5-dimethylpyrrolidine. The solution is heated for several days and then solvent and 2,5-dimethylpyrrolidine are removed by evaporation. The residue is taken up in a suitable solvent and washed with dilute aqueous base, dried over anhydrous sodium sulfate, filtered and concentrated. The residue is dissolved in hot isopropyl alcohol and reacted with fumaric acid to give the title compound.

EXAMPLE 15

8-[2-(2-Methyl-1-pyrrolidinyl)ethyl]-6,7,8,9-tetrahydro-6-methyl-5H-pyrido[3,2-c]azepin-5-one To a solution of 8-(2-chloroethyl)-6,7,8,9-tetrahydro-6-methyl-5H-pyrido[3,2-c]azepin-5-one in ethanol was added 2-methylpyrrolidine. The solution is heated to reflux for several hours and ethanol is removed by evaporation. The residue is partitioned between dilute aqueous base and chloroform and the chloroform layer concentrated and the title compound isolated by an appropriate technique, e.g., distillation.

EXAMPLE 16

8-[2-(1H-Pyrazol-1-yl)ethyl]-6,7,8,9-tetrahydro-6-methyl-5H-pyrido[3,2-c]azepin-5-one

To a suspension of sodium hydride in dimethylformamide (DMF) is added a solution of pyrazole in DMF. This solution is then added to a solution of 8-(2-chloroethyl)-6,7,8,9-tetrahydro-6-methyl-5H-pyrido[3,2-c]azepin-5-one in DMF. After reaction has occurred, DMF is removed by evaporation (80° C., vacuum pump) and the residue is taken up in chloroform. The chloroform solution is washed with dilute aqueous sodium hydroxide, dried over anhydrous sodium sulfate and concentrated by rotary evaporation (70° C., water aspirator). The residue is subjected to high pressure liquid chromatography using a suitable solvent on a silica gel column.

EXAMPLE 17

8-[2-(1H-Imidazol-1-yl)ethyl]-6,7,8,9-tetrahydro-6-methyl-5H-pyrido[3,2-c]-azepin-5-one

To a solution of 8-(2-chloroethyl)-6,7,8,9-tetrahydro-6-methyl-5H-pyrido[3,2-c]azepin-5-one in dimethylformamide (DMF) is added imidazole. The solution is heated to about 130° C. for several hr. DMF is removed by evaporation in vacuo and the residue is taken up in chloroform. The chloroform solution is washed with dilute aqueous sodium hydroxie, dried over anhydrous sodium sulfate and concentrated on a rotary evaporator to give the title compound.

EXAMPLE 18

8-[2-(4-Methyl-1-piperazinyl)ethyl]-6,7,8,9-tetrahydro-6-methyl-5H-pyrido[3,2-c]-azepin-5-one fumarate

N-methyl piperazine and 8-(2-chloroethyl)-6,7,8,9-tetrahydro-6-methyl-5H-pyrido[3,2-c]azepin-5-one are reacted in ethanol at reflux for several hr. Ethanol is removed by evaporation (90° C., water aspirator) and N-methyl piperazine is removed at 90° C. with a vacuum pump. The residue is dissolved in chloroform. The chloroform solution is dried, filtered and concentrated and the residue is reacted with fumaric acid in isopropyl alcohol to give crystalline title product.

EXAMPLE 19

8-[2-[4-[bis(4-Fluorophenyl)methyl]-1-piperidinyl]ethyl]-6,7,8,9-tetrahydro-6-methyl-5H-pyrido[3,2-c]-azepin-5-one hydrochloride

4-[Bis(4-fluorophenyl)methyl]piperidine and 8-(2-chloroethyl)-6,7,8,9-tetrahydro-6-methyl-5H-pyrido[3,2-c]azepin-5-one in ethanol are reacted by heating to reflux for about 20 hr. The solution is concentrated on a rotary evaporator and the residue is partitioned between aqueous dilute base and chloroform. The chloroform layer is dried over anhydrous sodium sulfate and concentrated. The residue is chromatographed by high pressure liquid chromatography using ethyl acetate and triethylamine over silica. After concentrating the desired fraction, the residue is converted to the hydrochloride salt in isopropyl alcohol using hydrogen chloride.

EXAMPLE 20

8-[2-(2,5-Dihydro-1H-pyrrol-1-yl)ethyl]-6,7,8,9-tetrahydro-6-methyl-5H-pyrido[3,2-c]azepin-5-one fumarate

A solution of 8-(2-chloroethyl)-6,7,8,9-tetrahydro-6-methyl-5H-pyrido[3,2-c]azepin-5-one in dimethylformamide (DMF) and a mixture of 3:1, v/v of 3-pyrroline:pyrrolidine in dimethylformamide is heated at about 65° C. overnight. The free base of the title compound is separated out by high pressure liquid chromatography using an appropriate solvent and reacted with fumaric acid in isopropyl alcohol to give the title compound.

EXAMPLE 21

8-[2-(1-Azetidinyl)ethyl]-6,7,8,9-tetrahydro-6-methyl-5H-pyrido[3,2-c]azepin-5-one oxalate

A solution of 8-(2-chloroethyl)-6,7,8,9-tetrahydro-6-methyl-5H-pyrido[3,2-c]azepin-5-one in 50 ml of dimethylformamide (DMF) is added a solution/suspension of sodium hydride in oil and DMF, and a solution of azetidine in DMF. The solution is stirred under nitrogen atmosphere until hydrogen evolution ceases. The solution is stirred further at room temperature for about 18 hr. Solvent is removed under reduced pressure and the residue is taken up in chloroform. The chloroform solution is washed with dilute aqueous base, dried over anhydrous sodium sulfate, filtered and concentrated. The residue is reacted with oxalic acid in isopropyl alcohol to give the oxalate salt.

EXAMPLE 22

8-[2-(1-Azetidinyl)ethyl]-6,7,8,9-tetrahydro-3-chloro-6-methyl-5H-pyrido[3,2-c]azepin-5-one oxalate

Following the procedure of Example 21, 3-chloro-8-(2-chloroethyl)-6,7,8,9-tetrahydro-6-methyl-5H-pyrido[3,2-c]azepin-5-one and azetidine are reacted and the free base of the title is isolated and reacted with oxalic acid.

EXAMPLE 23

8-]2-(1-Azetidinyl)ethyl]-6,7,8,9-tetrahydro-3-bromo-6-methyl-5H-pyrido[3,2-c]azepin-5-one oxalate

Following the procedure of Example 21, 3-bromo-8-(2-chloroethyl)-6,7,8,9-tetrahydro-6-methyl-5H-pyrido[3,2-c]azepin-5-one and azetidine are reacted and the free base of the title is isolated and reacted with oxalic acid.

EXAMPLE 24

8-[2-(1-Azetidinyl)ethyl]-6,7,8,9-tetrahydro-2-chloro-6-methyl-5H-pyrido[3,2-c]azepin-5-one oxalate

Following the procedure of Example 21, 2-chloro-8-(2-chloroethyl)-6,7,8,9-tetrahydro-6-methyl-5H-pyrido[3,2-c]azepin-5-one and azetidine are reacted and the free base of the title is isolated and reacted with oxalic acid.

EXAMPLE 25

8-[2-(Cyclopropylamino)ethyl]-6,7,8,9-tetrahydro-6-methyl-5H-pyrido[3,2-c]azepin-5-thione oxalate

To a solution of 8-(chloroethyl)-6,7,8,9-tetrahydro-6-methyl-5H-pyrido[3,2-c]azepin-5-thione in dimethyl sulfoxide is added crushed potassium carbonate and cyclopropylamine. The mixture is stirred for 2–3 days at room temperature. The reaction mixture is poured into water and extracted with benzene. The combined extracts are washed with water, dried over anhydrous sodium sulfate, filtered and concentrated by rotary evaporation. The residue is taken up in 1N hydrochloric acid and washed with methylene chloride. The aqueous layer is made just basic with concentrated sodium hydroxide and extracted with methylene chloride. The extract is dried, filtered, concentrated and purified using preparative HPLC using 1% triethylamine and methylene chloride. Like fractions are combined and reacted with fumaric acid in isopropyl alcohol.

EXAMPLE 26

8-[2-(1-Piperazinyl)ethyl]-6,7,8,9-tetrahydro-6-methyl-5H-pyrido[3,2-c]azepin-5-one oxalate The title compound is obtained by heating 8-(2-chloroethyl)-6,7,8,9-tetrahydro-6-methyl-5H-pyrido[3,2-c]azepin-5-one hydrochloride in excess piperazine. Excess piperazine is removed under reduced pressure (rotary evaporator) and the free base is isolated by solvent extraction and isolated and converted to the oxalate salt as in Example 11.

EXAMPLE 27

6-Methyl-8-[2-(1H-pyrrol-1-yl)ethyl]-6,7,8,9-tetrahydro-5H-pyrido[3,2-c]azepin-5-one fumarate Following the procedure of Example 20 and reacting a solution of 8-(2-chloroethyl)-6,7,8,9-tetrahydro-6-methyl-5H-pyrido[3,2-c]azepine-5-one in DMF with a solution of pyrrole in DMF gives the free base of the title compound, which is reacted with fumaric acid to give the title compound.

TABLE 3

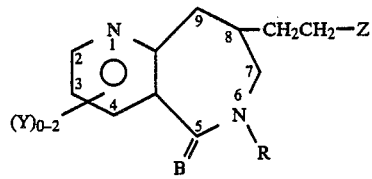

| Example No. | Y | B | R | Z | Salt |
|---|---|---|---|---|---|
| 1 | — | O | —CH₃ | —N(CH₃)₂ | fumarate |
| 2 | — | S | —CH₃ | —N(CH₃)₂ | fumarate |
| 3a | 3-Cl | O | —CH₃ | —N(CH₃)₂ | fumarate |
| 3b | 3-CH₃ | O | —CH₃ | —N(CH₃)₂ | fumarate |
| 3c | 2-Cl | O | —CH₃ | —N(CH₃)₂ | fumarate |
| 3d | 3-NO₂ | O | —CH₃ | —N(CH₃)₂ | fumarate |
| 3e | 3-(CH₃)₂N— | O | —CH₃ | —N(CH₃)₂ | fumarate |
| 3f | 3-C₆H₅— | O | —CH₃ | —N(CH₃)₂ | fumarate |
| 3g | — | O | —C₂H₅ | —N(CH₃)₂ | fumarate |
| 3h | — | O | —C₆H₁₁ | —N(CH₃)₂ | fumarate |
| 3i | — | O | C₆H₅—CH₂— | —N(CH₃)₂ | fumarate |
| 3j | — | O | 4-Cl—C₆H₄—CH₂— | —N(CH₃)₂ | fumarate |
| 3k | — | O | 4-OCH₃—C₆H₄—CH₂— | —N(CH₃)₂ | fumarate |
| 5 | — | O | —CH₃ | —NHCH₃ | fumarate |
| 6 | — | O | —CH₃ | 4-morpholinyl | fumarate |
| 7 | — | O | —CH₃ | | HCl |
| 8 | — | O | —CH₃ | | — |
| 9 | — | O | —CH₃ | 1-pyrrolidinyl | fumarate |
| 10 | — | O | —CH₃ | —N(C₄H₉)₂ | oxalate |
| 11 | — | O | —CH₃ | 1-piperdinyl | oxalate |
| 12 | — | O | —CH₃ | —N(CH₃)(C₆H₅CH₂—) | maleate |
| 13 | — | O | —CH₃ | —N(CH₃)(C₆H₅) | — |
| 14 | — | O | —CH₃ | 2,5-dimethyl-1-pyrrolidinyl | fumarate |
| 15 | — | O | —CH₃ | 2-methyl-1-pyrrolidinyl | — |
| 16 | — | O | —CH₃ | | — |
| 17 | — | O | —CH₃ | | — |

TABLE 3-continued

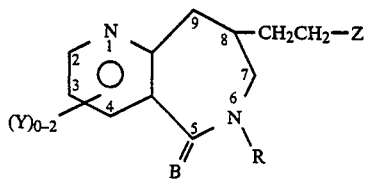

| Example No. | Y | B | R | Z | Salt |
|---|---|---|---|---|---|
| 18 | — | O | —CH$_3$ | 4-methyl-1-piperazinyl | fumarate |
| 19 | — | O | —CH$_3$ | —N⟨ ⟩—CH(4F—C$_6$H$_4$—)$_2$ | HCl |
| 20 | — | O | —CH$_3$ | —N⟨ ⟩ | fumarate |
| 21 | — | O | —CH$_3$ | 1-azetidinyl | oxalate |
| 22 | 3-Cl | O | —CH$_3$ | 1-azetidinyl | oxalate |
| 23 | 3-Br | O | —CH$_3$ | 1-azetidinyl | oxalate |
| 24 | 2-Cl | O | —CH$_3$ | 1-azetidinyl | oxalate |
| 25 | — | S | —CH$_3$ | cyclopropylamino | fumarate |
| 26 | — | O | —CH$_3$ | 1-piperazinyl | oxalate |
| 27 | — | O | —CH$_3$ | —N⟨ ⟩ | fumarate |

TABLE 4

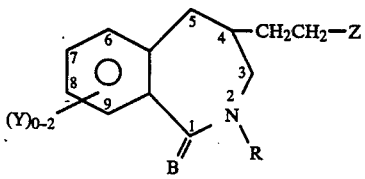

| Example No. | Y | B | R | Z | Salt |
|---|---|---|---|---|---|
| (4a) | — | O | —CH$_3$ | —N(CH$_3$)$_2$ | fumarate |
| (4b) | 8-Cl | O | —CH$_3$ | —N(CH$_3$)$_2$ | fumarate |
| (4c) | 8-CH$_3$ | O | —CH$_3$ | —N(CH$_3$)$_2$ | fumarate |
| (4d) | 7-Cl | O | —CH$_3$ | —N(CH$_3$)$_2$ | fumarate |
| (4e) | 7-NO$_2$ | O | —CH$_3$ | —N(CH$_3$)$_2$ | fumarate |
| (4f) | 8-N(CH$_3$)$_2$ | O | —CH$_3$ | —N(CH$_3$)$_2$ | fumarate |
| (4g) | 8-C$_6$H$_5$ | O | —CH$_3$ | —N(CH$_3$)$_2$ | fumarate |

PHARMACEUTICAL COMPOSITIONS

The invention further provides pharmaceutical compositions for administration to a living animal body comprising, as active ingredients, at least one of the compounds of Formula I according to the invention in association with a pharmaceutical carrier or excipient. The compounds are thus presented in a therapeutic composition suitable for oral, rectal, parenteral, subcutaneous, intramuscular, intraperitoneal, intravenous, or intranasal administration. Thus, for example, compositions for oral administration can take the form of elixirs, capsules, tablets or coated tablets containing pharmaceutical carriers or excipients conveniently used in the pharmaceutical art. Suitable pharmaceutical tableting carriers or excipients include lactose, potato and maize starches, talc, gelatin, stearic and silicic acids, magnesium stearate and polyvinyl pyrrolidone.

For parenteral administration, the pharmaceutical carrier or excipient can be comprised of a sterile parenterally acceptable liquid, e.g., water or arachis oil contained in ampoules.

In compositions for rectal administration, the pharmaceutical carrier can be comprised of a suppository base, e.g., cocoa butter or a glyceride.

Application to the nose, throat or bronchial region can be in the form of gargle or an aerosol spray containing small particles of the agent of Formula I in a spray or dry powder form.

Advantageously, the compositions are formulated as dosage units, each unit being adapted to supply a fixed dose of active ingredients. Tablets, coated tablets, capsules, ampoules and suppositories are examples of preferred dosage forms according to the invention. It is only necessary that the active ingredient constitute an effective amount, i.e., such that a suitable effective dosage will be consistent with the dosage form employed. The exact individual dosages, as well as daily dosages, will of course be determined according to standard medical principles under the direction of a physician or veterinarian. Generally, the pharamcology tests on guinea pigs in comparison to certain other antihistaminic drugs suggest an effective dose will be in the range of 1 to 50 mg for the more active compounds.

Based on the animal data, unit dosages containing an amount of compound equivalent to about 0.01 to about 1.0 mg of active drug per kilogram of body weight are contemplated. Daily dosages of about 0.04 to 4.0 mg/kg body weight are contemplated for humans and obviously several small unit dosage forms may be administered at one time. However, the scope of the invention is not to be limited by these contemplations due to uncertainty in transposing from animal data to humans.

Examples of unit dosage compositions are as follows:

| Capsules | | |
|---|---|---|
| Ingredients | Per Capsule | Per 1000 Capsules |
| 1. Active ingredient | 4 mg | 4.0 g |
| 2. Lactose | 150 mg | 150.0 g |
| 3. Magnesium stearate | 4 mg | 4.0 g |

Procedure for Capsules:
Step 1. Blend ingredients No. 1, No. 2 and No. 3 briefly.
Step 2. Pass the blend prepared in Step 1 through a No. 30 mesh screen (0.59 mm).
Step 3. Reblend screened blend from Step 2 until blend is uniform.
Step 4. Fill blend from Step 3 into No. 1 hard capsule shells.

| Tablets | | |
|---|---|---|
| Ingredients | Per Tablet | Per 1000 Tablets |
| 1. Active ingredient | 4 mg | 4 g |
| 2. Corn starch | 20 mg | 20 g |
| 3. Alginic acid | 20 mg | 20 g |
| 4. Sodium alginate | 20 mg | 20 g |
| 5. Magnesium stearate | 1.3 mg | 1.3 g |

Procedure for Tablets:
Step 1. Blend ingredients No. 1, No. 2, No. 3 and No. 4 in a suitable mixer.
Step 2. Add sufficient water portionwise to the blend from Step 1 with careful stirring after each addition. Such additions of water and stirring continued until the mass is of a constituency to permit its conversion to wet granules.
Step 3. The wet mass from Step 2 is converted to granules by passing it through an oscillating granulator using a No. 8 mesh (2.38 mm) screen.
Step 4. The wet granules from Step 3 are then dried in an oven at 140° C., until dry.
Step 5. The dry granules from Step 4 are lubricated by blending with ingredient No. 5 (magnesium stearate).
Step 6. The lubricated granules from Step 5 are compressed on a suitable table press.

| Intramuscular Injection | | |
|---|---|---|
| Ingredients | Per ml | Per Liter |
| 1. Active ingredient | 10.0 mg | 10.0 g |
| 2. Isotonic buffer solution pH 4.0 | q.s. to 1.0 ml | 1.0 liter |

Procedure:
Step 1. Dissolve active ingredient No. 1 in the buffer solution No. 2.
Step 2. Aseptically filter the solution from Step 1.
Step 3. The sterile solution from Step 2 is now aseptically filled into sterile ampuls.
Step 4. The ampuls prepared in Step 3 are sealed under aseptic condition.

| Suppositories | | |
|---|---|---|
| Ingredients | Per Supp. | Per 100 Supp. |
| 1. Active ingredient | 10.0 mg | 10.0 g |
| 2. Polyethylene Glycol 1000 | 1350.0 mg | 1350.0 g |
| 3. Polyethylene Glycol 4000 | 450.0 mg | 450.0 g |

Procedure:
Step 1. Melt ingredients No. 2 and No. 3 together and stir until uniform.
Step 2. Dissolve ingredient No. 1 in the molten mass from Step 1 and stir until uniform.
Step 3. Pour the molten mass from Step 2 into suppository molds and chill.
Step 4. Remove the suppositories from molds and wrap.

Therapeutic compositions for combatting histamine in unit dosage form, comprising a pharmaceutical carrier and an effective amount of a compound of Formula I or a pharmaceutically acceptable salt thereof are therefore an embodiment of this invention.

Various modifications and equivalents will be apparent to one skilled in the art and may be made in the compounds, methods, processes and pharmaceutical compositions of the present invention without departing from the spirit and scope thereof, and it is therefore to be understood that the invention is to be limited only by the scope of the appended claim.

What is claimed is:

1. A compound selected from the group having the formula:

wherein
A represents an aromatic ring selected from benzo when Q is carbon and from pyrido[3,2-c] when Q is nitrogen, either of which rings may be optionally substituted by one or two Y radicals, the same or different, selected from the group consisting of halo, loweralkyl, loweralkoxy, diloweralkylamino, nitro, phenyl and trifluoromethyl;
B is selected from oxygen and sulfur;
R is selected from the group consisting of loweralkyl, cycloalkyl and phenyl-loweralkyl, wherein phenyl may be optionally substituted by one or two radicals, the same or different, selected from halo, loweralkyl, loweralkoxy, nitro and trifluoromethyl;
Z is selected from the group consisting of $-NR^1R^2$, 1H-pyrazol-1-yl and 1H-imidazol-1-yl;
$R^1$ and $R^2$ may be the same or different and are selected from the group consisting of loweralkyl, cycloalkyl having 3-9 carbon atoms and phenyl-loweralkyl, wherein phenyl may be optionally substituted by 1 or 2 radicals, the same or different, selected from halo, loweralkyl, loweralkoxy, nitro, trifluoromethyl and cyano; or
$R^1$ and $R^2$ together with the adjacent nitrogen atom may form a heterocyclic ring structure selected from the group consisting of 1-azetidinyl, 1-pyrrolidinyl, 2,5-dimethyl-1-pyrrolidinyl, 2-methyl-1- pyrrolidinyl, 1-piperidinyl, 4-substituted-1-piperidinyl, 4-[bis(4-fluorophenyl)methyl]-1-piperidinyl, 4-morpholinyl, 1-piperazinyl, 4-substituted-1-piperazinyl, 1,2,3,6-tetrahydopyridin-1-yl, 1H-pyrrol-1-yl and 2,5-dihydro-1H-pyrrol-1-yl; the ooptical isomers thereof and pharmaceutically acceptable salts thereof.

2. The compound 8-[2-(dimethylamino)ethyl]-6,7,8,9-tetrahydro-6-methyl-5H-pyrido[3,2-c]azepin-5-one or a pharmaceutically acceptable salt thereof.

3. The compound 8-[2-(dimethylamino)ethyl]-6,7,8,9-tetrahydro-6-methyl-5H-pyrido[3,2-c]azepine-5-thione or a pharmaceutically acceptable salt thereof.

4. A method of counteracting histamine in a living animal body, which method comprises administering to said animal body an effective amount of a compound selected from the group having the fomula:

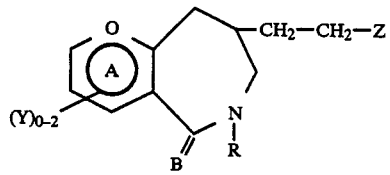

wherein

A represents an aromatic ring selected from benzo when Q is carbon and from pyrido[3,2-c] when Q is nitrogen, either of which rings may be optionally substituted by one or two Y radicals, the same or different, selected from the group consisting of halo, loweralkyl, loweralkoxy, diloweralkylamino, nitro, phenyl and trifluoromethyl;

B is selected from oxygen and sulfur;

R is selected from the group consisting of loweralkyl, cycloalkyl and phenylloweralkyl, wherein phenyl may be substituted by one or two radicals, the same or different, selected from halo, loweralkyl, loweralkoxy, nitro and trifluoromethyl;

Z is selected from the group consisting of $-NR^1R^2$, 1H-pyrazol-1-yl and 1H-imidazol-1-yl;

$R^1$ and $R^2$ may be the same or different and are selected from the group consisting of loweralkyl, cycloalkyl having 3–9 carbon atoms and phenyl-loweralkyl, wherein phenyl may be optionally substituted by 1 or 2 radicals, the same or different, selected from halo, loweralkyl, loweralkoxy, nitro, trifluoromethyl and cyano; or $R^1$ and $R^2$ together with the adjacent nitrogen atom may form a heterocyclic ring structure selected from the group consisting of 1-azetidinyl, 1-pyrrolidinyl, 2,5-dimethyl-1-pyrrolidinyl, 2-methyl-1-pyrrolidinyl, 1-piperidinyl, 4-substituted-1-piperidinyl, 4-[bis(4-fluorophenyl)methyl]-1-piperidinyl, 4-morpholinyl, 1-piperazinyl, 4-substituted-1-piperazinyl, 1,2,3,6-tetrahydopyridin-1-yl, 1H-pyrrol-1-yl and 2,5-dihydro-1H-pyrrol-1-yl; the optical isomers thereof and pharmaceutically acceptable salts thereof.

5. The method of claim 4 wherein the compound used is
8-[2-(dimethylamino)ethyl]-6,7,8,9-tetrahydro-6-methyl-5H-pyrido[3,2-c]azepin-5-one or a pharmaceutically acceptable salt thereof.

6. The method of claim 4 wherein the compound used is
8-[2-(dimethylamino)ethyl]-6,7,8,9-tetrahydro-6-methyl-5H-pyrido[3,2-c]azepine-5-thione or a pharmaceutically acceptable salt thereof.

7. A pharmaceutical composition suitable for counteracting histamine comprising:
(a) An effective amount of a compound selected from the group having the formula:

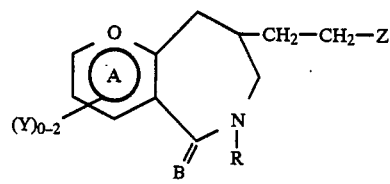

wherein

A represents an aromatic ring selected from benzo when Q is carbon and from pyrido[3,2-c] when Q is nitrogen, either of which rings may be optionally substituted by one or two Y radicals, the same or different, selected from the group consisting of halo, loweralkyl, loweralkoxy, diloweralkylamino, nitro, phenyl and trifluoromethyl;

B is selected from oxygen and sulfur;

R is selected from the group consisting of loweralkyl, cycloalkyl and phenyl-loweralkyl, wherein phenyl may be optionally substituted by one or two radicals, the same or different, selected from halo, loweralkyl, loweralkoxy, nitro and trifluoromethyl;

Z is selected from the group consisting of $-NR^1R^2$, 1H-pyrazol-1-yl and 1H-imidazol-1-yl;

$R^1$ and $R^2$ may be the same or different and are selected from the group consisting of loweralkyl, cycloalkyl having 3–9 carbon atoms and phenyl-loweralkyl, wherein phenyl may be optionally substituted by 1 or 2 radicals, the same or different, selected from halo, loweralkyl, loweralkoxy, nitro, trifluoromethyl and cyano; or $R^1$ and $R^2$ together with the adjacent nitrogen atom may form a heterocyclic ring structure selected from the group consisting of 1-azetidinyl, 1-pyrrolidinyl, 2,5-dimethyl-1-pyrrolidinyl, 2-methyl-1-pyrrolidinyl, 1-piperidinyl, 4-substituted-1-piperidinyl, 4-[bis(4-fluorophenyl)methyl]-1-piperidinyl, 4-morpholinyl, 1-piperazinyl, 4-substituted-1-piperazinyl, 1,2,3,6-tetrahydopyridin-1-yl, 1H-pyrrol-1-yl or 2,5-dihydro-1H-pyrrol-1-yl, the optical isomers thereof and pharmaceutically acceptable salts thereof;
(b) a pharmaceutical carrier therefor.

8. The pharmaceutical composition of claim 7 wherein the compound is
8-[2-(dimethylamino)ethyl]-6,7,8,9-tetrahydro-6-methyl-5H-pyrido[3,2-c]azepin-5-one or a pharmaceutically acceptable salt thereof.

9. The pharmaceutical composition of claim 7 wherein the compound used is 8-[2-(dimethylamino)ethyl]-6,7,8,9-tetrahydro-6-methyl-5H-pyrido[3,2-c]azepine-5-thione or a pharmaceutically acceptable salt thereof.

* * * * *